(12) United States Patent
Liao et al.

(10) Patent No.: US 9,688,838 B1
(45) Date of Patent: Jun. 27, 2017

(54) DIISONONYL TEREPHTHALATE PLASTICIZER AND ITS USE AS WELL AS PROCESS FOR PRODUCING THE SAME

(71) Applicant: NAN YA PLASTICS CORPORATION, Taipei (TW)

(72) Inventors: Te-Chao Liao, Taipei (TW); Jung-Jen Chuang, Taipei (TW); Chung-Yu Chen, Taipei (TW); Hsun-Min Lin, Taipei (TW)

(73) Assignee: NAN YA PLASTICS CORPORATION (TW)

( * ) Notice: Subject to any disclaimer, the term of this patent is extended or adjusted under 35 U.S.C. 154(b) by 0 days.

(21) Appl. No.: 15/155,104

(22) Filed: May 16, 2016

(51) Int. Cl.
    C08K 5/00    (2006.01)
    C08K 5/12    (2006.01)
    C07C 67/08   (2006.01)
    C07C 69/82   (2006.01)

(52) U.S. Cl.
    CPC ............... C08K 5/12 (2013.01); C07C 67/08 (2013.01); C07C 69/82 (2013.01)

(58) Field of Classification Search
    CPC .................................. C08K 5/00; C08K 5/12
    See application file for complete search history.

(56) References Cited

U.S. PATENT DOCUMENTS

2010/0305255 A1* 12/2010 Grass ................. C08K 5/12
                                                            524/296

* cited by examiner

Primary Examiner — Robert Harlan
(74) Attorney, Agent, or Firm — Bacon & Thomas, PLLC

(57) ABSTRACT

A diisononyl terephthalate (DINT) plasticizer is synthesized by esterifying an isononanol mixture composed of multiple alcohols with pure terephthalic acid in the presence of an esterification catalyst, and the DINT plasticizer due to featuring a low plasticizer migration below 1.4% and a low glass transition temperature below −75° C. is so suitable for making those soft plastic products, such as hoses, wires, cables, exercise mats, table mats, playing balls or disposable gloves, required for having a high content of plasticizers more than 70 PHR.

10 Claims, No Drawings

DIISONONYL TEREPHTHALATE PLASTICIZER AND ITS USE AS WELL AS PROCESS FOR PRODUCING THE SAME

BACKGROUND OF THE INVENTION

1. Technical Field

The present invention relates to a diisononyl terephthalate (DINT) suitably used as a plasticizer and if used in plastic products having a property of low plasticizer migration, and more particularly relates to a process for producing the DINT plasticizer.

2. Description of Related Art

Plasticizers have been extensively used in the plastic industry such as functionally used as coating materials, filling and reinforcing material, and processing aids. Thermoplastics effectively promote physical effects via plasticizers added thereto, since plasticizers when dissolved in thermoplastics form a Homogeneous phase, and provide swelling effects. As compared to thermoplastics without plasticizers added, those thermoplastics having plasticizers added enjoy advantages including said thermoplastics are processed under much lower processing temperature and said thermoplastics are allowed to become more excellent in better flowability when heated for molding as well as more favorite in both elasticity improved and rigidity reduced.

Plasticizers are extensively used as long as their use is odorless, colorless, UV resistant, cold-resistant, heat-resistant, hydrolysis-resistant, flame-retardant, less volatile and safe to human health as the final products require. In addition, manufacturing of plasticizers is required to be simple and environmental friendly, and preferably does not generate undesired by-products and polluted wastewater.

An esterified product synthesized from acids and alcohols may be used to produce a plasticizer. Therein, the acids include dicarboxylic acid and polycarboxylic acid, and the alcohols include straight- or branched-chain alcohols having 6-13 carbons as well as may be a single compound or a mixture.

In a basic process for producing an esterified product, acids or acid anhydrides and alcohols or mixed alcohols react in the presence of an acid (e.g. sulfuric acid) as a catalyst for esterification. During synthesis, the reactive alcohols have to be used in an excess amount, and the acid acting as the catalyst is such controlled during synthesis that it does not cause the esterified product to have undesirable smell or poor hue. Therefore, the process requires mild reaction conditions and multiple purifying steps.

According to current technical level, catalysts often used for synthesizing the ester plasticizer are metal-containing esterification catalysts, including tin-containing, titanium-containing or zirconium-containing esterification catalysts, and tin-containing, titanium-containing or zirconium-containing salts, oxides and dissoluable organic compounds. Metallic catalysts of this type are esterification catalysts used at a temperature higher than 180° C., such as tin powder, tin oxide, organic titanate, and organic zirconates (including tetrabutyl zirconate, alkyl titanate, titanium chelate, etc.).

There are two ways to prepare the ester plasticizer, namely esterification and hydrogenization. U.S. Pat. No. 6,310,235B1 discloses a method for preparing the ester plasticizers through esterification, wherein an acid (such as dicarboxylic acid or polycarboxylic acid or acid anhydride) and an alcohol perform esterification in the presence of a titanium-containing or zirconium-containing or tin-containing metal catalyst. The esterification is carried out in two stages. In the first stage, the temperatures to be employed is relatively low (120-160° C.) for forming a monoester. Then the temperature is raised to 250° C. and a catalyst is added for bis-esterification. Afterward, neutralization is performed using an alkali-containing or alkali-earth-metal-containing aqueous hydroxide solution, follows by removing excess reactive alcohol, drying and filtering, so as to obtain an esterified product used to produce a plasticizer. Nevertheless, such a process for esterification is disadvantageous for requiring relatively long reaction time.

The plasticizers commonly used today include phthalate-type plasticizers such as diisooctyl phthalate (DIOP) plasticizers, diisononyl phthalate (DINP) plasticizers and di(2-ethylhexyl) terephthalate (DOTP) plasticizer. However, according to the relevant literatures, phthalate-containing plasticizers may generate environmental hormone that can cause great danger to organisms and their environment.

While a di(2-ethylhexyl) terephthalate (DOTP) plasticizer is acceptable in terms of environmental protection and has a glass transition temperature (Tg) of −82° C., it tends to migrate to the surface of the final products (hereinafter referred to as plasticizer migration), particularly when it is used in manufacturing of soft PVC products that requires large use of plasticizers. When final PVC products require an amount of plasticizer to reach 70 PHR, the plasticizer migration rate is greater than 2.5%, leading to degraded appearance of the final PVC products.

SUMMARY OF THE INVENTION

Regarding a plasticizer possessing the lower plasticizer migration rate is the more suitable to use in making a soft plastic product is obviously a common knowledge for person having ordinary skill in the art.

In view of this, it is a primary objective of the present invention to provide a diisononyl terephthalate (DINT) plasticizer not only synthesized from an invented isononanol mixture (abbreviated as INA), but also provided with an excellent plasticizer migration lower than other terephthalates when used as a plasticizer for use in making soft plastic products required for using a large amount of plasticizers (such as more than 70 PHR); wherein the invented isononanol mixture (INA) contains at least the following components (a)-(g), summing up to 100 mol %:
(a) isoocty lalcohol: 0.1-0.25 mol %;
(b) methylpropylpentanol: 0.03-0.3 mol %;
(c) 2-methyl octanol: 30-35 mol %;
(d) dimethyl heptanol 10-15 mol %;
(e) 5-methyl octanol: 50-55 mol %;
(f) n-nonanol: 1-5 mol %; and
(g) isodecanol: 1.5-2.5 mol %.

It is another objective of the present invention to provide a diisononyl terephthalate (DINT) plasticizer, when used for making soft plastic products required for using a large amount of plasticizers (such as more than 70 PHR), exhibits an outstanding low plasticizer migration below 1.4%, which is so significantly superior to those existing plasticizers commonly used in the state of art.

It is a yet another object of the present invention to provide a process for producing diisononyl terephthalate (DINT) plasticizer not only to exclude use of phthalate acids or acid anhydrides but also to exhibit a low plasticizer migration when used for making soft plastic products, which producing process involves steps of using pure terephthalic acids (PTA) and an isononanol mixture (INA) as starting materials, performing an esterification reaction in the presence of titanium, tin or an inorganic-acid catalyst, performing neutralization with an alkali-containing aqueous hydroxide solution, removing excess reactive alcohols, and performing drying, filtration and purification, to obtain an esterified product of diisononyl terephthalate used as a DINT plasticizer having a glass transition temperature (Tg) below −75° C. and so excellent in high purity and good hue as well as having a low plasticizer migration superior to those existing plasticizers in the art.

It is still another object of the present invention to provide a process for producing diisononyl terephthalate (DINT) plasticizer, comprising the following steps:

1) undergoing a single-stage esterification reaction in a reactor to obtain a reaction mixture (or reactant) by reacting purified terephthalic acids (PTA) or its derivatives 23-35% by weight of the reactant with an isononanol mixture (INA) 65-77% by weight of the reactant in the presence of a metal-containing catalyst or an inorganic-acid catalyst as an esterification catalyst 0.1-6.0% by weight of the reactant at temperature of 200-250° C. and pressure of 5-760 mbar for 9-16 hours, until the reactant has its acid value smaller than 1 mgKOH/g;
2) neutralizing the reactant of step 1) with an alkali-containing aqueous hydroxide solution that contains 5-20 wt % of a hydroxide mixture, until the reactant has its acid value smaller than 0.07 mgKOH/g, and
3) removing excess alcohols, drying and filtering of the reactant of step 2) to obtain an esterified product of diisononyl terephthalate (DINT) for use in making as a DINT plasticizer.

In accordance with another aspect of the present invention, there is provided a diisononyl terephthalate (DINT) plasticizer has both well-defined quality and processing properties as comparable with those existing terephthalate-containing plasticizers (e.g. DOTP plasticizers) commonly used in the art. Additionally, when used for making soft plastic products requiring use of plasticizers having an amount more than 70 PHR, the disclosed diisononyl terephthalate (DINT) plasticizer exhibits a lower plasticizer migration rate of equal to or smaller than 1.4%, however still so superior to DOTP plasticizers.

Moreover, the disclosed diisononyl terephthalate (DINT) plasticizer is much safer to organisms and their environment, and more particularly serves as a good substitute for either phthalate-containing plasticizers (e.g. DOP plasticizers) or terephthalate-containing plasticizers (e.g. DOTP plasticizers).

DETAILED DESCRIPTION OF THE INVENTION

In the present invention, a process for producing an esterified product of diisononyl terephthalate (or a diisononyl terephthalate plasticizer) is disclosed to use pure terephthalic acids (PTA) and an isononanol mixture (INA) as starting material for esterification, instead of using phthalate acid and acid anhydride, and further disclosed to use a metal-containing catalyst or an inorganic-acid catalyst as an esterification catalyst. In the presence of the esterification catalyst, performing an esterification reaction on said pure terephthalic acid reacted with the isononanol mixture (INA), so as to obtain the esterified product of diisononyl terephthalate (or the DINT plasticizer).

Therein, the isononanol mixture (INA) contains at least the following components (a)-(g), summing up to 100 mol %:
(a) isoocty lalcohol: 0.1-0.25 mol %;
(b) methylpropylpentanol: 0.03-0.3 mol %;
(c) 2-methyl octanol: 30-35 mol %;
(d) dimethyl heptanol 10-15 mol %;
(e) 5-methyl octanol: 50-55 mol %;
(f) n-nonanol: 1-5 mol %; and
(g) isodecanol: 1.5-2.5 mol %.

The methylpropylpentanol used in the isononanol mixture (INA) must be limited to have an effective amount ranged between 0.03 mol % and 0.3 mol %, the reason is that the use amount of said methylpropylpentanol if either smaller than 0.03 mol % or greater than 0.3 mol %, the resultant DINT plasticizer exhibits a plasticizer migration rate higher than 1.4% when used for making soft plastic products requiring use of the plasticizers at 70 PHR or more.

Likewise, the isodecanol used in the isononanol mixture (INA) must be limited to have an effective amount ranged between 1.5 mol % and 2.5 mol %, since the use amount of said isodecanol is used either smaller than 1.5 mol % or greater than 2.5 mol %, the resultant DINT plasticizer also exhibits a plasticizer migration rate higher than 1.4% when used for making soft plastic products requiring use of the plasticizers at 70 PHR or more.

The methylpropylpentanol may be one or more selected from the group consisting of 1-methyl-1-propylpentanol, 1-methyl-2-propylpentanol, 1-methyl-3-propylpentanol, 1-methyl-4-propylpentanol, 1-methyl-5-propylpentanol, 2-methyl-1-propylpentanol, 2-methyl-2-propylpentanol, 2-methyl-3-propylpentanol, 2-methyl-4-propylpentanol, 2-methyl-5-propylpentanol, 3-methyl-1-propylpentanol, 3-methyl-2-propylpentanol, 3-methyl-3-propylpentanol, 3-methyl-4-propylpentanol, 3-methyl-5-propylpentanol, 4-methyl-1-propylpentanol, 4-methyl-2-propylpentanol, 4-methyl-3-propylpentanol, 4-methyl-4-propylpentanol, 4-methyl-5-propylpentanol, 5-methyl-1-propylpentanol, 5-methyl-2-propylpentanol, 5-methyl-3-propylpentanol, 5-methyl-4-propylpentanol and 5-methyl-5-propylpentanol.

In the disclosed process for producing the esterified product of diisononyl terephthalate (or the DINT plasticizer), the catalyst for esterification is used in an amount equal to 0.1-6.0 wt % based on the total amount of the materials for synthesis, and the catalyst may be an inorganic acid catalyst or a metal catalyst. Therein, the inorganic acid catalyst may be one or more selected from the group consisting of sulfuric acid, boric acid, phosphoric acid, perchloric acid and p-toluenesulfonic acid; while the metal catalyst may be one or more selected from the group consisting of tin octoate, tetraisopropyl titanate (TIPT) and tetraisobutyl titanate (TIBT).

In the disclosed process for producing the esterified product of diisononyl terephthalate (or the DINT plasticizer), all the materials for synthesizing pure terephthalic acid (PTA) or its derivative and the isononanol mixture (INA) have to be stoichiometrically measured. Particularly, the amount of alcohols introduced is 0.1-1.0 mol more than that of the acid.

In the disclosed process for producing the esterified product of diisononyl terephthalate (or the DINT plasticizer), a single-step with high-temperature esterification may be used. In the presence of an esterification catalyst, pure terephthalic acid (PTA) or its derivative reacts with isononanol mixture (INA) for esterification to synthesize a DINT plasticizer.

According to the present invention, a process for producing the esterified product of diisononyl terephthalate (or the DINT plasticizer) comprises the following steps:
1) taking purified terephthalic acid (PTA) or its derivative and an isononanol mixture (INA) as starting materials by satisfying a molar ratio of the terephthalic acid (PTA) or the derivative to the isononanol mixture (INA) ranged between 1:2.2 and 1:3.8 for an esterification reaction; or alternatively, replaced by satisfying a weight ratio of 23-35% of the terephthalic acid to 65-77% of the isononanol mixture by weight of a reaction mixture (or reactant) obtained from the esterification reaction, respectively;

2) based on the total weight of the reactant, taking 0.1-6 wt % of a metal-containing catalyst or an inorganic-acid catalyst as an esterification catalyst;

3) in the presence of the esterification catalyst of Step 2) performing a single-step esterification reaction at a reaction pressure of 5-760 mbar and a reaction temperature of 200-250° C., preferably, at pressure of 15-700 mbar and temperature of 220-240° C., to obtain a produced reactant in a reactor by reacting the terephthalic acid or its derivative with the isononanol mixture of Step 1) for 9-16 hours, until the reactant has its acid value smaller than 1 mgKOH/g; and 4) upon completion of the reaction, neutralizing the reactant of step 3) with an alkali-containing aqueous hydroxide solution that contains 5-20 wt % of a hydroxide mixture, and when the reactant has its acid value smaller than 0.07 mgKOH/g; and 5) removing excess alcohols, drying and filtering of the reactant of step 4) to obtain the esterified product of diisononyl terephthalate (or the DINT plasticizer).

In the disclosed process for producing the esterified product of diisononyl terephthalate (or the DINT plasticizer), water has to be removed from the reaction system. Water formed is removed together with the reactive alcohols from the reaction system as an azeotrope at an azeotropic temperature of 90-180° C. When the reaction takes place to the extent that the reactant has its acid value becoming below 1 mgKOH/g, in the reaction tank includes, in addition to the diisononyl terephthalate to be synthesized, there are partially esterified dicarboxylic acid, excess reactive alcohols and the catalyst.

In the disclosed process for producing the esterified product of diisononyl terephthalate (or the DINT plasticizer), esterification is followed by neutralization. An alkali-containing aqueous hydroxide solution is taken as a neutralizing agent to neutralize the acid surviving esterification into salts. The neutralizing agent has a concentration of 5-25 wt %, and preferably 9-16 wt %. The amount of the neutralizing agent to be used is equal to 4-5 times of the acid value of the reactant. The alkali-containing aqueous hydroxide solution is preferably an aqueous sodium hydroxide solution, which produces salts depositing as solid crystals after neutralization that can be easily removed at a later stage of the process.

When neutralization takes place to the extent that the reactant has its acid value becoming below 0.07 mgKOH/g, distillation is carried out to decrease the content of alcohols to 300 ppm or lower and to make the hydrolysis compound formed from the catalyst after hydrolysis (abbreviated as hydrolyzed catalyst) easy to be separated off through filtration. It can be advantageous to either introduce water vapors or add a high surface area adsorbent, e.g. activated carbon, to the reactant in order to aid the removal of the hydrolyzed catalyst.

After excess reactive alcohols are removed, drying and filtration are performed. Drying may be carried in the reaction tank with or without introduction of an inert gas, such as nitrogen gas. The crude ester is then filtered to free it of carboxylic acids, hydrolysis products of the catalyst and the adsorbent. The filtration is carried out at room temperature or at a raised temperature. The filtration can also be aided by customary filter aids such as cellulose, kieselguhr or wood powder.

In the disclosed process for producing the esterified product of diisononyl terephthalate (or the DINT plasticizer), filtration or purification is carried out at room temperature or at a temperature below 100° C. Then the salts as products of neutralization, metal salts from the catalyst, and impurities are filtered off, so as to obtain the desired DINT plasticizer. In particular, the purified DINT plasticizer has its purity higher than 99.8%, with its hue as high as 10 APHA, making it a competent plasticizer.

Diisononyl terephthalate (DINT) prepared according to the present invention is a synthesized product made from the isononanol mixture (INA) containing multiple components with no phthalate acid used in its preparation. When act as a DINT plasticizer, it is comparable with phthalate-containing plasticizers such as DOP and DINP in terms of quality and processing property. When used in plastic products, it exhibits a plasticizer migration rate superior to that of dioctyl terephthalate (DOTP). Particularly, for plastic products requiring use of plasticizers of 70 PHR or more, the disclosed DINT plasticizer has its plasticizer migration rate below 1.4%, making it perfect for soft PVC products that requires high ratio of plasticizers (more than 70 PHR). For example, it is perfect for soft PVC products such as hoses, wires and cables, exercise mats, table mats, playing balls, gloves, and so on.

The following Examples and Comparative Examples are provided for explaining the effects of the present invention, and shall form no limitations to the scope of the present invention.

Ester plasticizers prepared according to the following Examples and Comparative Examples through esterification were measured for their acid value (mgKOH/g), purity (%), hue (APHA) and processing properties by following the protocols given below.

1. Acid Value (mgKOH/g):

Method ASTM D1045 is used to an acid value test.

2. Purity (%):

Gas chromatography (GC) is used to a purity test.

3. Hue (APHA):

Color (Pt-co unit) is used to a hue (APHA) test.

4. Processing Properties:

Specimens by way of the following formulas are tested, respectively:

Formula (A) is prepared by PVC of 100 PHR, plasticizer of 40 PHR, and Ba—Zn stabilizer of 2 PHR.

Formula (B) is prepared by PVC of 100 PHR, plasticizer of 70 PHR, and Ba—Zn stabilizer of 2 PHR.

The homogeneous mixture of Formula (A) or Formula (B) was processed in a roller mill for 5 minutes at 175° C. to form thin sheet of a thickness of 0.4 mm.

The sheets of Formula (A) were used in tests for five processing properties including initial coloring, heat resistance, transparency, plasticized coefficient, and tensile strength, while the sheets of both Formulas (A) and Formula (B) were tested for their plasticizer migration rate.

a. Measurement for Initial Coloring:

The 0.4 mm sheets of Formula (A) were preheated in a pressure apparatus at 185° C. for 3 minutes, then heated for 3 minutes, and cooled for 3 minutes, so as to form a sheet having a thickness of 4 mm, which was then tested for yellowness using a spectrophotometer (MS-020 PLUS).

b. Measurement for Heat Resistance:

The 0.4 mm sheet of Formula (A) was cut into specimens having a size with 25 cm in length, 1.5 cm in width and 0.2 cm in thickness, which were then tested for heat resistance in an automatic testing oven (Metrtrastat PSD-260) with conditions of 180° C. for 2 hours.

c. Measurement for Plasticizer Migration Rate:

The 0.4 mm sheets of Formulas (A) and Formulas (B) were cooled and cut into pieces having a size with 5 cm in length and 5 cm in width, respectively.

PVC rigid tapes sized with 5 cm in length and 5 cm in width and having a given weight were attached to the pieces, and the pieces and tapes were sandwiched by flat glass plates from above and below. A load of 3 kg was placed on the combination before it was tested in an oven with conditions of 100° C. for 24 hours.

Plasticizer migration of the formulas were compared by:

migration permeability %=$(Y-X)/X \times 100$, where X is the given weight of the rigid PVC tape, and
Y is the weight of the rigid PVC tape after permeation.

d. Measurement for Transparency:

The 0.4 mm sheets of Formula (A) were preheated in a pressure apparatus at 185° C. for 3 minutes, then heated for 3 minutes, and cooled for 3 minutes, so as to form a sheet having a thickness of 4 mm, which was then tested for transparency using a gloss-haze meter (VGS-300A).

e. Measurement for Plasticized Coefficient:

Specimens were made from the 0.4 mm sheet of Formula (A) as used for transparency testing. The specimens were compressed into 6 mm specimens under heat. The specimens were put into contact with a durometer for 15 seconds and the readings were recorded. Then the records were compared to the hardness-PHR scale, and plasticized coefficient was calculated using the following equation.

Plasticized Coefficient=Specimen Quantity/DOP Quantity.

f. Measurement for Tensile Strength:

The 0.4 mm sheet of Formula (A) was cut into dumbbell-shaped specimens, which were then tested for tensile strength using a universal test machine (SHIMADZU AG-X) at a tensile speed of 200 mm/min.

g. Measurement for Glass Transition Temperature (Tg):

The plasticizer was weighed for 5-10 mg for glass transition temperature (Tg) testing using a Differential Scanning calorimeter, or DSC (TA-2100).

Example 1

Following the formula as shown in Table 1, 119 g of pure terephthalic acid (PTA) and 311 g of an isononanol mixture (containing 0.2 mol % of 2-methyl-2-propylpentanol and 1.4 mol % of isodecanol; supplied by Nan Ya Plastics Corp.), together with 0.71 g of a catalyst TIPT (tetraisopropyl titanate) were simultaneously fed into a four-neck flask.

With introduction of nitrogen gas, reaction was carried out under 5-760 mbar for 9 hours at 225° C. Water formed in the reaction was removed. When the reaction took place to the extent that a reactant had its acid value becoming below 1 mgKOH/g, neutralization was performed using an alkali-containing aqueous hydroxide solution. When the reactant had its acid value becoming below 0.07 mgKOH/g, distillation was carried out to reduce alcohols to 300 ppm. Then after filtration or purification, an esterified product of diisononyl terephthalate was obtained and used as a DINT plasticizer.

The DINT plasticizer such produced was tested regarding both physical properties and processing properties, and the test results are given in Table 1, including hue of 10 APHA, acid value of 0.05 mgKOH/g, and purity if 99.8%. According to the DSC-based glass transition temperature (Tg) test, Tg equals to −76° C., and the measured plasticizer migration rate is 1.25% (hereinafter the expression simplified into migration rate: 1.25%). Also measured includes transparency: 89.5% and plasticized coefficient: 1.1.

Example 2

The method described in Example 1 was followed and the formula shown in Table 1 was used. The isononanol mixture (containing 0.2 mol % of 2-methyl-2-propylpentanol and 1.4 mol % of isodecanol; supplied by Nan Ya Plastics Corp.) was replaced with a different isononanol mixture (containing 0.03 mol % of 2-methyl-2-propylpentanol and 1.4 mol % of isodecanol; supplied by Nan Ya Plastics Corp.). Under the same processing conditions, a DINT plasticizer was produced.

The DINT plasticizer such produced was tested regarding both physical properties and processing properties, and the test results are given in Table 1, including hue: 10 APHA, acid value: 0.06 mgKOH/g, purity: 99.8%, Tg: −76° C., migration rate: 1.35% (at 70 PHR), transparency: 89.5%, and plasticized coefficient: 1.1.

Example 3

The method described in Example 1 was followed and the formula shown in Table 1 was used. The isononanol mixture (containing 0.2 mol % of 2-methyl-2-propylpentanol and 1.4 mol % of isodecanol; supplied by Nan Ya Plastics Corp.) was replaced with a different isononanol mixture (containing 0.3 mol % of 2-methyl-2-propylpentanol and 1.4 mol % of isodecanol; supplied by Nan Ya Plastics Corp.). Under the same processing conditions, a DINT plasticizer was produced.

The DINT plasticizer such produced was tested regarding both physical properties and processing properties, and the test results are given in Table 1, including hue: 10 APHA, acid value: 0.06 mgKOH/g, purity: 99.6%, Tg: −76° C., migration rate: 1.3% (at 70 PHR), transparency: 89.4%, and plasticized coefficient: 1.1.

Example 4

The method described in Example 1 was followed and the formula shown in Table 1 was used. The isononanol mixture (containing 0.2 mol % of 2-methyl-2-propylpentanol and 1.4 mol % of isodecanol; supplied by Nan Ya Plastics Corp.) was replaced with a different isononanol mixture (containing 0.2 mol % of 2-methyl-2-propylpentanol and 1 mol % of isodecanol; supplied by Nan Ya Plastics Corp.). Under the same processing conditions, a DINT plasticizer was produced.

The DINT plasticizer such produced was tested regarding both physical properties and processing properties, and the test results are given in Table 1, including hue 10 APHA, acid value 0.06 mgKOH/g, purity: 99.7%, Tg: −76° C., migration rate: 1.38% (at 70 PHR), transparency: 89.4%, and plasticized coefficient: 1.1.

Example 5

The method described in Example 1 was followed and the formula shown in Table 1 was used. The isononanol mixture (containing 0.2 mol % of 2-methyl-2-propylpentanol and 1.4 mol % of isodecanol; supplied by Nan Ya Plastics Corp.)

was replaced with a different isononanol mixture (containing 0.2 mol % of 2-methyl-2-propylpentanol and 2.5 mol % of isodecanol; supplied by Nan Ya Plastics Corp.). Under the same processing conditions, a DINT plasticizer was produced.

The DINT plasticizer such produced was tested regarding both physical properties and processing properties, and the test results are given in Table 1, including hue: 10 APHA, acid value: 0.06 mgKOH/g, purity: 99.7%, Tg: −76° C., migration rate: 1.4% (at 70 PHR), transparency: 89.5%, and plasticized coefficient:

Example 6

The method described in Example 1 was followed and the formula shown in Table 1 was used. The isononanol mixture (containing 0.2 mol % of 2-methyl-2-propylpentanol and 1.4 mol % of isodecanol; supplied by Nan Ya Plastics Corp.) was replaced with a different isononanol mixture (containing 0.2 mol % of 3-methyl-1-propylpentanol and 1.4 mol % of isodecanol; supplied by Nan Ya Plastics Corp.). Under the same processing conditions, a DINT plasticizer was produced.

The DINT plasticizer such produced was tested regarding both physical properties and processing properties, and the test results are given in Table 1, including hue 10 APHA, acid value 0.06 mgKOH/g, purity: 99.8%, Tg: −76° C., migration rate: 1.26% (at 70 PHR), transparency: 89.5%, and plasticized coefficient: 1.1.

Comparative Example 1

Following the formula as shown in Table 1, 120 g of pure terephthalic acid (PTA), 280 g of isooctanol (2EH), and 0.6 g of catalyst TIPT (tetraisopropyl titanate) were simultaneously fed into a four-neck flask. With introduction of nitrogen gas, reaction was carried out under 5-760 mbar for 8 hours at 225° C. Water formed in the reaction was removed. When the reaction took place to the extent that a reactant had its acid value becoming below 1 mgKOH/g, neutralization was performed using an alkali-containing aqueous hydroxide solution. When the reactant had its acid value becoming below 0.07 mgKOH/g, distillation was carried out to reduce alcohols to 300 ppm. Then after filtration or purification, an esterified product of dioctyl terephthalate (DOTP) was obtained and used as a DOTP plasticizer.

The DOTP plasticizer so produced exhibited physical properties and processing properties in relevant tests as shown in Table 1, including hue: 10 APHA, acid value: 0.06 mgKOH/g, purity: 99.7%, Tg: −82° C., migration rate: 2.5% (at 70 PHR), transparency: 89.2%, and plasticized coefficient: 1.05.

Comparative Example 2

The method described in Example 1 was followed and the formula shown in Table 1 was used. The isononanol mixture was replaced with a different isononanol mixture containing 0.4 mol % of 2-methyl-2-propylpentanol. Under the same processing conditions, a DINT plasticizer was produced.

The DINT plasticizer so produced exhibited physical properties processing properties in relevant tests as shown in Table 1, including hue 12 APHA, acid value 0.06 mgKOH/g, purity: 99.8%, Tg: −75° C., and migration rate: 1.5% (at 70 PHR).

Comparative Example 3

The method described in Example 1 was followed and the formula shown in Table 1 was used. The alcohols were replaced with an isononanol mixture (free from 2-methyl-2-propylpentanol, isodecanol and its derivative; supplied by Evonik Industries). Under the same processing conditions, a DINT plasticizer was produced.

The DINT plasticizer so produced exhibited physical properties and processing properties in relevant tests as shown in Table 1, including hue 12 APHA, acid value 0.06 mgKOH/g, purity: 99.7%, Tg: −74° C., and migration rate: 1.8% (at 70 PHR).

Comparative Example 4

The method described in Example 1 was followed and the formula shown in Table 1 was used. The alcohols were replaced with an isononanol mixture (containing 0.2 mol % of 2-methyl-2-propylpentanol and 2.6 mol % of isodecanol). Under the same processing conditions, a DINT plasticizer was produced.

The DINT plasticizer so produced exhibited physical properties and processing properties in relevant tests as shown in Table 1, including a hue of 12 APHA, an acid value of 0.05 mgKOH/g, a purity of 99.8%, Tg: −74° C., and migration rate: 1.7% (at 70 PHR).'

Comparative Example 51

The method described in Example 1 was followed and the formula shown in Table 1 was used. The alcohols were replaced with an isononanol mixture (containing 0.2 mol % of 2-methyl-2-propylpentanol and 0.8 mol % of isodecanol). Under the same processing conditions, a DINT plasticizer was produced.

The DINT plasticizer so produced exhibited physical properties processing properties in relevant tests as shown in Table 1, including hue 13 APHA, acid value 0.05 mgKOH/g, purity: 99.8%, Tg: −74° C., and migration rate: 1.6% (at 70 PHR).

Results:

1. Examples 1-6 produced DINT plasticizers from pure terephthalic acid (PTA) and isononanol (INA) mixtures of different compositions. Among these plasticizers, the one produced in Example 1 using the isononanol mixture containing 0.2 mol % of 2-methyl-2-propylpentanol and 1.4 mol % of isodecanol exhibited the best plasticizer migration rate of 1.25%.

By comparison, when tested specimens containing plasticizer used at a level more than 70 PHR, all of the plasticizers of Comparative Example 1-5 exhibited a plasticizer migration rate higher than 1.4%.

2. Example 1 teaches to use the isononanol (INA) mixture reacted with the pure terephthalic acid (PTA) to obtain an esterified product of diisononyl terephthalate.

Comparative Example 1 teaches to use the isooctanol (2EH) reacted with the pure terephthalic acid (PTA) to obtain an esterified product of dioctyl terephthalate.

By comparison, the DINT plasticizer of Example 1 has a plasticizer migration rate of 1.25%, superior to that of the DOTP ester plasticizer of Comparative Example 1 of 2.5%. This proves that the DINT plasticizer synthesized from the isononanol (INA) mixture when used as a DINT plasticizer is more effective than the DOTP plasticizer synthesized from 2EH in improving the plasticizer migration rate at a high plasticizer content that is 70 PHR or more. When used for making PVC products, it prevents the PVC products from surface migration of the plasticizer, thereby contributing to even appearance and smooth touch.

3. Example 1 and Comparative Example 3 teaches to use the pure terephthalic acid (PTA) respectively reacted with the isononanol (INA) mixtures with different compositions to synthesize DINT plasticizers.

By comparison, the DINT plasticizer of Example 1 made from the isononanol mixture (containing 0.2 mol % of 2-methyl-2-propylpentanol and 1.4 mol % of isodecanol, supplied by Nan Ya Plastics Corp.) exhibited a plasticizer migration rate of 1.25%, superior to that of the DINT plasticizer of Comparative Example 3 of 1.8%.

4. When the plasticizer was used in an amount reaching 70 PHR, the plasticizer migration rates shown in Examples 1-6 were much better than those seen in Comparative Examples 1-5.

And, when the plasticizer was used in an amount reduced to 40 PHR, the plasticizer migration rates shown in Examples 1-6 remained better than those seen in Comparative Examples 1-3.

TABLE 1

| item | | Example | | | | | | Comparative Example | | | | |
|---|---|---|---|---|---|---|---|---|---|---|---|---|
| | | 1 | 2 | 3 | 4 | 5 | 6 | 1 | 2 | 3 | 4 | 5 |
| INA composition (mol %) | 2-methyl-2-propylpentanol | 0.2 | 0.03 | 0.3 | 0.2 | 0.2 | 0 | 0 | 0.4 | 0 | 0.2 | 0.2 |
| | 3-methyl-1-propylpentanol | 0 | 0 | 0 | 0 | 0 | 0.2 | 0 | 0 | 0 | 0 | 0 |
| | isodecanol | 1.4 | 1.4 | 1.4 | 1.0 | 2.5 | 1.4 | 0 | 1.4 | 0 | 2.6 | 0.8 |
| | others | 98.4 | 98.6 | 98.3 | 98.8 | 97.3 | 98.4 | 0 | 98.2 | 100 | 97.2 | 99 |
| Synthetic materials | PTA (g) | 119 | 119 | 119 | 119 | 119 | 119 | 120 | 119 | 119 | 119 | 119 |
| | 2EH (g) | 0 | 0 | 0 | 0 | 0 | 0 | 280 | 0 | 0 | 0 | 0 |
| | INA (g) | 311 | 311 | 311 | 311 | 311 | 311 | 0 | 311 | 311 | 311 | 311 |
| | TIPT (g) | 0.71 | 0.71 | 0.71 | 0.71 | 0.71 | 0.71 | 0.6 | 0.71 | 0.71 | 0.71 | 0.71 |
| Properties analysis | Acid value (mgKOH/g) | 0.05 | 0.06 | 0.06 | 0.06 | 0.06 | 0.06 | 0.06 | 0.06 | 0.06 | 0.05 | 0.05 |
| | Purity (%) | 99.8 | 99.8 | 99.6 | 99.7 | 99.7 | 99.8 | 99.7 | 99.8 | 99.7 | 99.8 | 99.8 |
| | Hue (APHA) | 10 | 10 | 10 | 10 | 10 | 10 | 10 | 12 | 12 | 12 | 13 |
| | Tg (° C.) | −76 | −76 | −76 | −76 | −76 | −76 | −82 | −75 | −74 | −74 | −74 |
| Analysis of processing properties | Initial coloring | fair | fair | fair | fair | fair | fair | fair | fair | fair | fair | fair |
| | Heat resistance | good | good | good | good | good | good | fair | fair | good | good | good |
| | Migration rate (%) 40 PHR | 0.2 | 0.23 | 0.22 | 0.24 | 0.24 | 0.21 | 0.28 | 0.25 | 0.29 | 0.24 | 0.24 |
| | 70 PHR | 1.25 | 1.35 | 1.3 | 1.38 | 1.4 | 1.26 | 2.5 | 1.5 | 1.8 | 1.7 | 1.6 |
| | Tensile strength | 276 | 277 | 275 | 275 | 274 | 276 | 274 | 273 | 275 | 276 | 274 |
| | Transparency | 89.5 | 89.5 | 89.4 | 89.4 | 89.5 | 89.5 | 89.2 | 89.4 | 89.1 | 89.3 | 89.4 |
| | Plasticized coefficient | 1.1 | 1.1 | 1.1 | 1.1 | 1.1 | 1.1 | 1.05 | 1.1 | 1.1 | 1.1 | 1.1 |

What is claimed is:

1. A process for producing a diisononyl terephthalate plasticizer, involving using a pure terephthalic acid or a derivative thereof and an isononanol mixture with a molar ratio of the terephthalic acid or the derivative to the isononanol mixture ranged between 1:2.2 and 1:3.8 as starting materials for an esterification reaction, and esterifying said terephthalic acid or its derivative and said isononanol mixture in the presence of an esterification catalyst selected from a metal-containing catalyst or an inorganic acid catalyst, to synthesize an esterified product of diisononyl terephthalate used as a plasticizer having a glass transition temperature (Tg) below −75° C.;
characterized in that said isononanol mixture is composed of the following components (a)-(g) to 100 mol %:
(a) isooctanol: 0.1-0.25 mol %;
(b) methylpropylpentanol: 0.03-0.3 mol %;
(c) 2-methyl octanol: 30-35 mol %;
(d) dimethyl heptanol: 10-15 mol %;
(e) 5-methyl octanol: 50-55 mol %;
(f) n-nonanol: 1-5 mol %; and
(g) isodecanol: 1.0-2.5 mol %.

2. The process for producing a diisononyl terephthalate plasticizer of claim 1, comprising the following steps:
1) undergoing a single-stage esterification reaction in a reactor to obtain a reaction mixture by reacting the purified terephthalic acids (PTA) or its derivatives 23-35% by weight of the reaction mixture with the isononanol mixture (INA) 65-77% by weight of the reaction mixture in the presence of the esterification catalyst 0.1-6.0% by weight of the reaction mixture at temperature of 200-250° C. and pressure of 5-760 mbar for 9-16 hours, until the reaction mixture has its acid value smaller than 1 mgKOH/g;
2) neutralizing the reaction mixture of step 1) with an alkali-containing aqueous hydroxide solution that contains 5-20 wt % of a hydroxide mixture, until the reaction mixture has its acid value smaller than 0.07 mgKOH/g, and
3) removing excess alcohols, drying and filtering of the reaction mixture of step 2) to obtain said diisononyl terephthalate (DINT) plasticizer having a glass transition temperature (Tg) below −75° C.

3. The process for producing a diisononyl terephthalate plasticizer of claim 2, wherein the inorganic acid catalyst is one or more selected from the group consisting of sulfuric acid, boric acid, phosphoric acid, perchloric acid and p-toluenesulfonic acid.

4. The process for producing a diisononyl terephthalate plasticizer of claim 2, wherein the metal-containing catalyst is one or more selected from the group consisting of tin octoate, tetraisopropyl titanate (TIPT) and tetraisobutyl titanate (TIBT).

5. The process for producing a diisononyl terephthalate plasticizer of claim 2, wherein said components (b) of methylpropylpentanol is one or more selected from the group consisting of 1-methyl-1-propylpentanol, 1-methyl-2-propylpentanol, 1-methyl-3-propylpentanol, 1-methyl-4-propylpentanol, 1-methyl-5-propylpentanol, 2-methyl-1-propylpentanol, 2-methyl-2-propylpentanol, 2-methyl-3-propylpentanol, 2-methyl-4-propylpentanol, 2-methyl-5-propylpentanol, 3-methyl-1-propylpentanol, 3-methyl-2-propylpentanol, 3-methyl-3-propylpentanol, 3-methyl-4-propylpentanol, 3-methyl-5-propylpentanol, 4-methyl-1-propylpentanol, 4-methyl-2-propylpentanol, 4-methyl-3-propylpentanol, 4-methyl-4-propylpentanol, 4-methyl-5-propylpentanol, 5-methyl-1-propylpentanol, 5-methyl-2-propylpentanol, 5-methyl-3-propylpentanol, 5-methyl-4-propylpentanol and 5-methyl-5-propylpentanol.

6. The process for producing a diisononyl terephthalate plasticizer of claim 2, wherein said isononanol mixture is composed of the following components (h)-(j) to 100 mol %:
 (h) 2-methyl-2 propylpentanol: 0.2 mol %,
 (i) isodecanol: 1.4 mol %; and
 (j) a mixture of isooctanol, 2-methyl octanol, dimethyl heptanol, 5-methyl octanol and n-nonanol: 98.4 mol %.

7. The process for producing a diisononyl terephthalate plasticizer of claim 2, wherein at step 2) an excess amount of the alkali-containing aqueous hydroxide used is equal to 4 to 5 times of the acid value of the reaction mixture of step 1).

8. The process for producing a diisononyl terephthalate plasticizer of claim 2, wherein the reaction mixture of step 2) after esterification is further by way of introducing water vapors or adding activated carbons to remove hydrolysis compounds formed from the esterification catalyst after hydrolysis from said reaction mixture.

9. A diisononyl terephthalate plasticizer, having a glass transition temperature (Tg) below −75° C. and made of the esterified product of diisononyl terephthalate obtained from claim 1.

10. A soft PVC product containing 100 PHR of PVC and at least 70 PHR of the diisononyl terephthalate plasticizer of claim 9, characterized in that the soft PVC product is one selected from the group consisting of a hoses, a wire, a cable, an exercise mat, a table mat, a playing ball and a disposable glove as well as has a plasticizer migration rate smaller than 1.4% resulted from the diisononyl terephthalate plasticizer.

* * * * *